United States Patent

Eisenfeld et al.

[11] Patent Number: 6,044,284
[45] Date of Patent: Mar. 28, 2000

[54] APPARATUS AND METHOD FOR MEASURING THE CONCENTRATION OF MECONIUM IN AMNIOTIC FLUID

[75] Inventors: Leonard I. Eisenfeld, 18 Faxon Dr., West Hartford, Conn. 06117; John Young Oh, Durham, N.C.

[73] Assignee: Leonard I. Eisenfeld, West Hartford, Conn.

[21] Appl. No.: 09/168,586

[22] Filed: Oct. 8, 1998

[51] Int. Cl.[7] .................................................. A61B 5/00
[52] U.S. Cl. ........................................... 600/310; 600/309
[58] Field of Search ................................... 600/309, 310, 600/340, 341, 322, 581

[56] References Cited

U.S. PATENT DOCUMENTS 5,713,351  2/1998  Billings et al. .......................... 600/309

OTHER PUBLICATIONS

Molcho et al., "Spectrophotometric Determination of Meconium Concentration in Amniotic Fluid," Journal of Biomedical Engineering, vol. 8, No. 2, pp. 162–165, Apr. 1986.

Primary Examiner—Eric F. Winakur
Attorney, Agent, or Firm—Cummings & Lockwood

[57] ABSTRACT

In an apparatus and method for measuring in vitro the concentration of meconium in amniotic fluid, a plurality of sensors are placed in predetermined locations throughout an amniotic sac. Each sensor includes a blue light-emitting diode having a peak transmission wavelength centered at about 430 nm, a transducer comprising a blue-enhanced photodiode for converting the light received from the light-emitting diode to a voltage signal, and an operational amplifier for amplifying the voltage signal. The light source and transducer are spaced a predetermined distance relative to each other, and define an amniotic fluid passageway therebetween for receiving the amniotic fluid. A microcontroller calculates, in accordance with an empirically-determined linear equation, the meconium concentration based on the natural log of each transducer signal. The transducer signals are continuously converted to meconium concentration readings, and generated on a display to provide a continuous, real-time, quantitative and/or qualitative assessment of the presence of, and concentration of meconium in a plurality of locations within the amniotic sac.

24 Claims, 5 Drawing Sheets

APPARATUS AND METHOD FOR MEASURING THE CONCENTRATION OF MECONIUM IN AMNIOTIC FLUID

FIELD OF THE INVENTION

The present invention relates to apparatus and methods for monitoring amniotic fluid, and more particularly, to apparatus and methods for optically monitoring the concentration of meconium in amniotic fluid.

BACKGROUND INFORMATION

Meconium is fetal stool, and when passed in utero, it may indicate or be associated with fetal stress. If the concentration of meconium in the amniotic sac is sufficiently high, the fetus may aspirate the meconium into the respiratory system and cause potentially-fatal complications in the airways and lungs.

To date, most clinical caretakers assess the concentration of meconium in amniotic fluid by visual inspection. In this type of analysis, the concentration of meconium is typically characterized as being "thin" (i.e., a relatively low concentration) or "thick" (i.e., a relatively high concentration). Amniotic fluid having a "thick" meconium concentration typically may have the consistency of pea soup and contain particulate matter.

During a typical labor, the amniotic fluid may not be visually inspected until released into the vaginal pool. As a result, there may be a significant time delay between the release of any meconium within the amniotic sac and its detection by the medical staff. In addition, the visual assessment of meconium concentration is a subjective determination, and depending upon the person rendering the assessment, the interpretation may vary and, in turn, lead to misdiagnoses.

One prior art approach to obtaining a more objective assessment of meconium content is described in Weitzner, J. S. et al., "Objective Assessment Of Meconium Content Of Amniotic Fluid", *Obstet Gynecol* (1990) 76: 1143–1145. The Weitzner et al. technique involves withdrawing amniotic fluid samples, spinning them within a centrifuge, and analyzing a meconium "crit".

U.S. Pat. No. 5,009,507 to Katz shows a method for evaluating meconium content in amniotic fluid wherein a sample of amniotic fluid is visually compared to a meconium concentration chart while transmitting fluorescent light through both the sample and the chart.

U.S. Pat. No. 5,514,598 to Doody shows a method for detecting prenatal meconium excretion by chromatographically separating proteins in a sample of the fluid, and analyzing the separated proteins for the presence of a meconium antigen.

Although these prior art approaches should provide a more objective assessment of meconium concentration than visual inspection, they do not allow for a real-time, continuous reading of the concentration of meconium in the amniotic sac. In addition, these prior art techniques tend to be relatively cumbersome and time consuming, require sophisticated and expensive equipment, and/or may not provide consistent results.

U.S. Pat. No. 5,361,759 to Genevier et al. ("the '759 patent") is directed generally to a non-invasive system for optically detecting in vivo the presence and concentration of meconium and/or blood in amniotic fluid. The system comprises a single probe having a body 32 for insertion into the uterus. The probe includes an optical cell 31 defining a passageway for permitting the flow of amniotic fluid therethrough, and a fiber optic bundle 33 optically connected to the passageway. The fiber optic bundle 33 includes two branches, one for transmitting light into the optical cell, and the other for collecting reflected light and conveying it to a spectrophotometer comprising a plurality of photodetectors. The light reflected off the amniotic fluid within the passageway is returned from the probe to second, third and fourth photodetectors to detect the reflectance values at the following three wavelengths of interest: (i) 405–420 nm (for meconium), (ii) 540 nm (for blood), and (iii) 700 nm (for a baseline). The concentration of meconium and blood is calculated based on the detected values at each wavelength.

One potential drawback of measuring the light reflected off the amniotic fluid as described in the '759 patent is that the intensity of the reflected light may be relatively weak, and therefore the apparatus may have a relatively low sensitivity, particularly within the clinically relevant range for assessing meconium thickness. The system of the '759 patent also requires multiple wavelengths, and appropriate shielding, particularly if the probe is placed, for example, against the uterine wall. These requirements can lead to additional complexity and expense. Another drawback of the approach described in the '759 patent is that the system employs only a single probe and sensor. The meconium concentration may vary from one location to another within the amniotic sac. Thus, the single probe of the '759 patent may accurately detect the absence of meconium, or a relatively low concentration of meconium at its particular location within the amniotic sac, but may not detect the presence of, or a dangerously high concentration of meconium at another location in the amniotic sac. In addition, the single probe employed in the system of the '759 patent may become clogged with relatively "thick" meconium and/or other particulate matter, and in turn become inoperative or otherwise fail to accurately monitor, or assess the concentration of meconium in the amniotic fluid.

U.S. Pat. No. 5,172,693 to Doody ("the '693 patent") shows another prior art system for in vivo, optical detection of meconium in amniotic fluid. The '693 patent does not teach inserting the probe into the amniotic fluid, but rather teaches placing a probe against the outside surface of the uterine wall (FIGS. 2 and 3). Light at selected wavelengths is transmitted through the uterine wall and into the amniotic fluid for exciting the fluorescent pigments of the meconium. The fluorescence emitted by the meconium pigments is detected, spectrally isolated, amplified, and analyzed to determine the presence of meconium in amniotic fluid. Thus, although the '693 patent shows a system for detecting the presence of meconium, it does not teach or suggest a system for measuring or otherwise obtaining a qualitative and/or quantitative assessment of the concentration of meconium in amniotic fluid.

Accordingly, it is an object of the present invention to overcome one or more of the above-described drawbacks and disadvantages of the prior art.

SUMMARY OF THE INVENTION

The present invention is directed to an apparatus and method for measuring meconium concentrations in amniotic fluid. The apparatus comprises at least one sensor including a light source, a transducer facing the light source and spaced a predetermined distance therefrom, and an amniotic fluid passageway defined between the light source and transducer for receiving amniotic fluid. The transducer generates first signals indicative of the amount of light from the light source transmitted through the amniotic fluid passageway and received by the transducer. A micro-controller is electrically coupled to the transducer for receiving the first signals therefrom, and generating based thereon second signals indicative of the concentration of meconium in the amniotic fluid received in the amniotic fluid passageway.

In accordance with a preferred method of the invention, the apparatus includes a plurality of sensors, the sensors are placed in a plurality of locations within an amniotic sac, and the second signals are generated indicative of the concentration of meconium in the amniotic fluid in a plurality of locations in the amniotic sac. Preferably, one sensor is located adjacent to, or near a fetus' nose or mouth, another sensor is located adjacent to, or near the fetus' anus, and another sensor is spaced between, or relative to the first two sensors, such as in the amniotic fluid bathing the fetus' body between the head and anus. In addition, one of the sensors also may be located in a portion of the amniotic sac where amniotic fluid, and any meconium in the amniotic fluid, would tend to settle due to gravitational forces.

Also in a preferred embodiment of the invention, the micro-controller includes a program defining an empirically-determined, approximately linear relationship between the natural log of the first sensor signals and the concentration of meconium in the amniotic fluid. The micro-controller calculates the natural log of each first sensor signal, and based on the empirically-determined, linear relationship, calculates the meconium concentration corresponding to each sensor signal.

Accordingly, one advantage of the apparatus and method of the invention is that it may provide a continuous, real-time, in vitro assessment of the presence of, and concentration of meconium in amniotic fluid. Yet another advantage of the invention is that the meconium concentration readings may be generated for a plurality of locations within an amniotic sac.

Other objects and advantages of the present invention will become apparent in view of the following detailed description of a preferred embodiment and accompanying drawings.

DETAILED DESCRIPTION OF A PREFERRED EMBODIMENT

Figure 1:
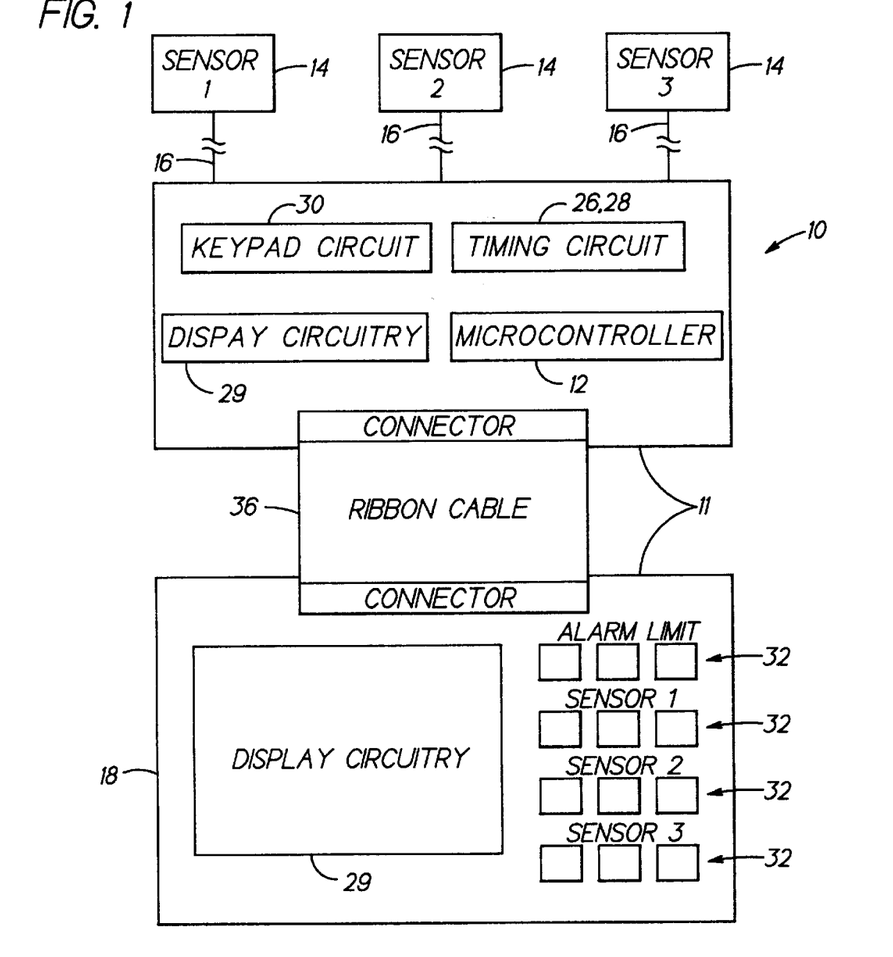
FIG. 1 is a schematic illustration of an apparatus embodying the present invention for measuring the concentration of meconium in amniotic fluid.

As shown in FIG. 1, an apparatus embodying the present invention for measuring the concentration of meconium in amniotic fluid is indicated generally by the reference numeral 10. The apparatus 10 comprises a control computer 11 coupled to a plurality of optical sensors 14. Each sensor 14 is an optoelectric sensor which transmits a voltage signal indicative of the amount of light transmitted by the sensor through the amniotic fluid received within a passageway of the sensor. Each sensor 14 is connected to the control computer 12 through a respective cable 16 in order to control actuation of the sensors and transmit the sensor signals to the computer. The control computer 11 includes a display 18 in order to display information based on the sensor signals indicative of the concentration of meconium in amniotic fluid.

Figure 2:
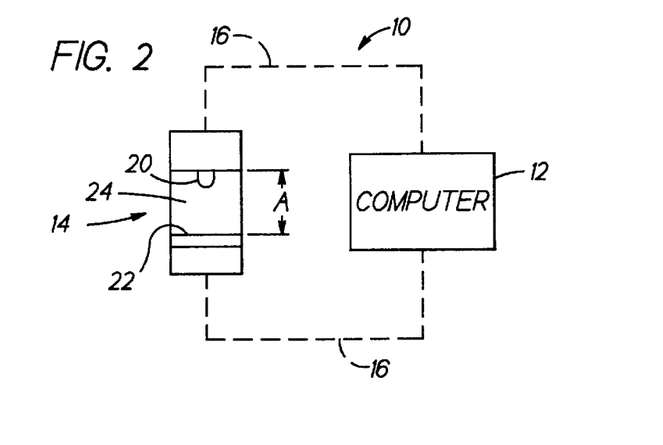
FIG. 2 is a schematic illustration of a typical sensor of the apparatus of FIG. 1 for transmitting to the control computer a voltage signal indicative of the concentration of meconium in the amniotic fluid received within the sensor passageway.

As shown in FIG. 2, each sensor 14 comprises a light source 20, a transducer 22 spaced a predetermined distance from the light source for generating a voltage signal indicative of the amount of light impinging thereon, and a fluid passageway 24 defined between the light source and transducer for permitting the passage of amniotic fluid therethrough and sensing the concentration of meconium in the fluid received within the passageway. As shown in FIG. 2, the light source 20 is spaced a predetermined distance "A" from the transducer 22 defining the width of the amniotic fluid passageway 24. Typically, for a given light source 20 and transducer 22, the smaller is the width "A", the stronger is the voltage signal generated by the transducer, and thus the greater is the sensitivity and range of the apparatus for detecting the presence of, and changes in meconium concentration levels. However, if the width "A" is too small, the passageway may become blocked or clogged with relatively "thick" meconium and/or other particulate matter and, in turn, prevent effective and/or accurate operation of the apparatus. In the currently-preferred embodiment of the invention, the width "A" is preferably within the range of approximately 1 through 5 mm. However, the width "A" may be varied within, or outside this range, depending upon the voltage levels employed, the desired sensitivity and range of the apparatus, and design considerations necessary to prevent clogging of the amniotic fluid passageways.

Figure 3:
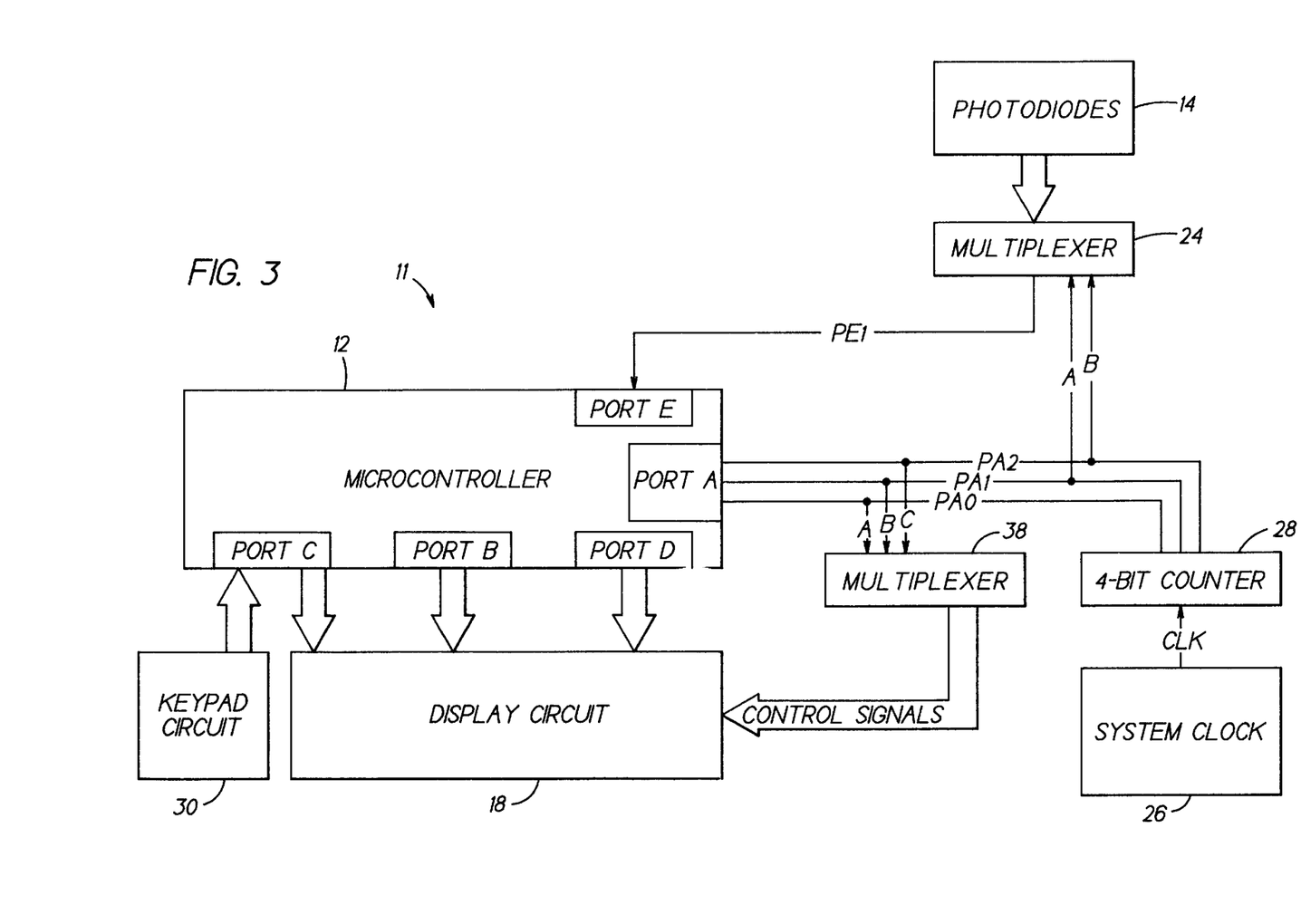
FIG. 3 is a schematic illustration of the micro-controller, display circuit and other select components of the control computer of FIG. 1.

Turning to FIG. 3, the control computer 11 preferably comprises a micro-controller 12, such as Motorola Model No. MC68HC11, which includes, among other desirable features, 40 I/O ports for controlling multiple peripheral devices, and an internal A/D converter facilitating the combination of analog and digital electronics, and for converting the analog signals transmitted by the transducers 22 into corresponding digital signals.

In the currently-preferred embodiment of the invention, each light source 20 is a blue light-emitting diode (LED) having a peak transmission wavelength centered at approximately 430 nm and a spectrum bandwidth of approximately 65 nm. Meconium possesses a broad absorption spectrum centered at about 410 nm, and therefore this type of light source provides a desirable radiation bandwidth for measuring the concentration of meconium in amniotic fluid.

Also in the currently-preferred embodiment of the invention, each transducer 22 comprises a blue-enhanced photodiode which converts the light received from the light source 20 into a voltage signal. Each photodiode 22 is connected to a respective operational amplifier (not shown) to improve the signal and the transducer's range. As is further described below, based on empirical data, the microcontroller 12 converts the voltage signals received from the sensors 14 into meconium concentration readings and displays the readings on the display 18. As may be recognized by those skilled in the pertinent art based on the teachings herein, numerous other types of light sources and transducers may be equally employed. For example, rather than mount an LED adjacent to each transducer, one or more LEDs or other light sources may be mounted remote from the transducers. The light source(s) may further include one or more fiber optic cables optically coupled between the LED (or other light source) and the amniotic fluid passageway. In this case, the distal end of each fiber optic cable may be mounted opposite to, and facing a respective transducer for transmitting the light through the respective passageway and onto the transducer.

As also shown in FIG. 3, the three sensors 14 are connected through a multiplexer 24 to the micro-controller 12. A timing circuit including a system clock 26 (e.g., a "555" timer) and counter 28 are connected to the multiplexer 24 and micro-controller 12 to ensure that the various electronic components of the system operate in sync with one another. In particular, the clock 26 and counter 28 control the muliplexer 24, and transmit signals to the micro-controller 12 (port "A") so that it can identify the sensor signals transmitted through the multiplexer to the micro-controller (port "B") and allow the micro-controller to, in turn, correctly match each sensor signal to its respective location on the display 18.

An input device in the form of a keypad 30 is connected to the micro-controller 12 to enable a user to input information or data and to control operation of the apparatus. In the currently-preferred embodiment of the invention, the keypad 30 enables a user to enter calibration information, and as described further below, an alarm limit. In addition, the keypad 30 can enable a user to stop and re-start the apparatus, monitor system functions, enter new calibration or alarm data, perform maintenance, and otherwise control operation of the apparatus in a desired manner. As will be recognized by those skilled in the pertinent art based on the teachings herein, any of numerous different types of input devices which are currently, or later become known, may be employed in combination with, or instead of the keypad 30.

Figure 4:
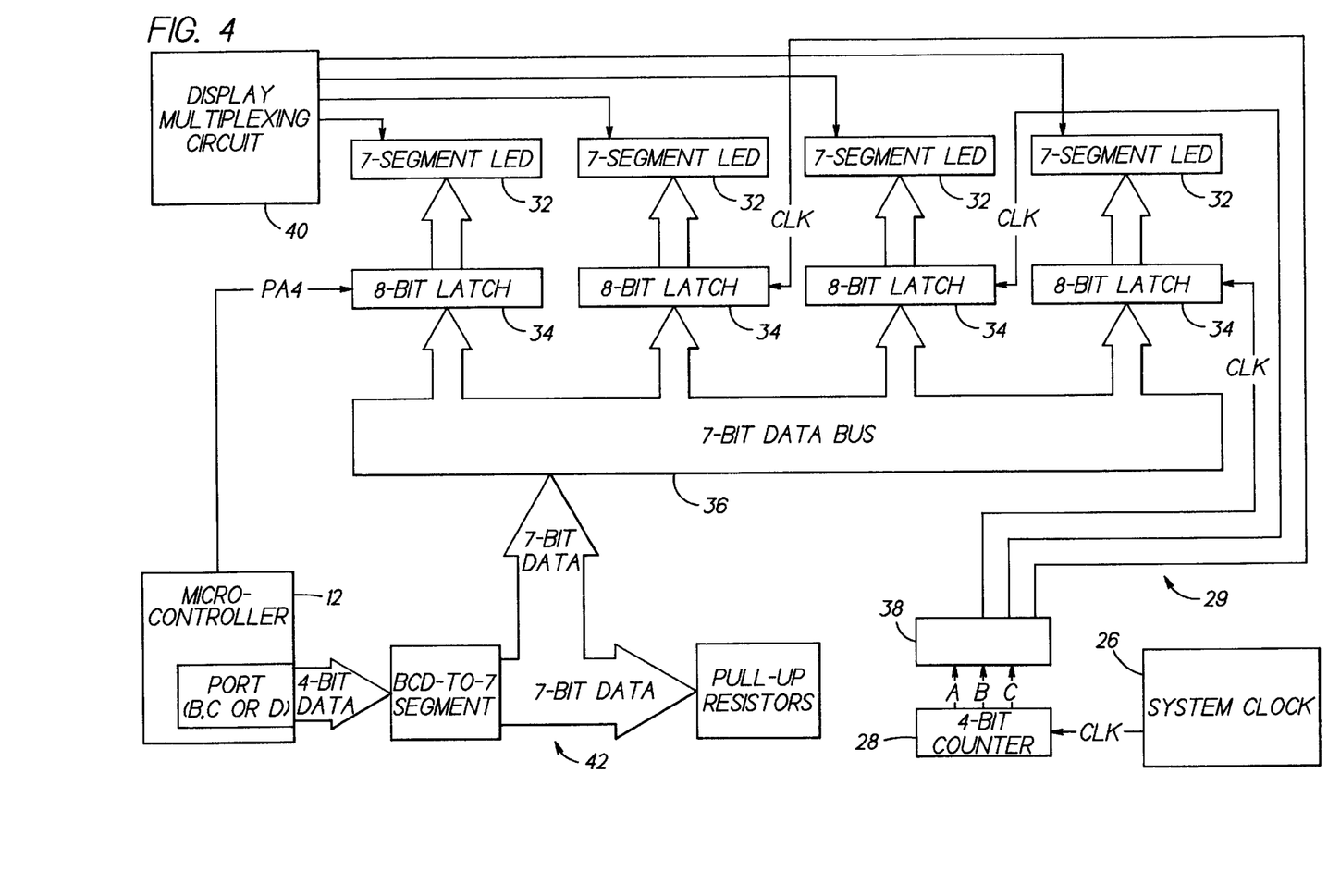
FIG. 4 is a schematic illustration of select components of the display circuit of the control computer of FIG. 1.

As shown in FIG. 4, a display circuit 29 of the apparatus 10 employs a plurality of seven-segment LED displays 32. One group of LED displays 32 is used to display information entered through the keypad 30, such as the alarm limit, and the other groups are each used to display meconium concentration readings generated based on the signals transmitted by a respective one of the three sensors 14. For the sake of clarity, only one 7-segment LED of each group 32 is illustrated in FIG. 4. However, as will be recognized by those skilled in the pertinent art based on the teachings herein, the additional LEDs of each group are connected to the display circuit in the same manner as each LED group illustrated. As also shown in FIG. 4, each LED display 32 is connected through a respective 8-bit latch 34 and a data bus 36 to the micro-controller 12. The system clock 26 and counter 28 control a multiplexer 38 to, in turn, control the latches 34 for the groups of displays 32 associated with the sensors 14, and thereby ensure that each group of LEDs 32 captures and displays the correct data. The latches 34 and associated group of LEDs 32 for the keypad display information, on the other hand, are connected to a respective port of the micro-controller 12. A display multiplexing circuit 40 is connected to each LED display 32 in order to turn the groups "on" and "off" in sequence, and therefore reduce the total "on-time" of each group. Appropriate processing electronics 42 are provided to convert the 4-bit data of the micro-controller 12 to 7-bit data in order to allow the LEDs 32 to read and display the data.

In the operation of the apparatus and method of the invention, the sensors 14 and cables 16 are inserted through catheters or like devices (not shown), and preferably a plurality of sensors are positioned at different sensor sites within the amniotic sac. As will be recognized by those skilled in the pertinent art based on the teachings herein, the number of sensor sites, and their locations within the amniotic sac may vary depending upon a number of considerations. Generally, however, the sensors 14 are placed at locations containing amniotic fluid, and which are of most interest to the medical staff for detecting the presence and concentration of meconium. Accordingly, although the apparatus 10 employs three sensors 14, only one or two sensors may be employed for certain patients, or if desired, the apparatus may be provided with more than three sensors.

In accordance with a currently-preferred embodiment of the invention, at least two sensors are employed in order (i) to provide redundancy in the event that one sensor becomes clogged or otherwise inoperative; (ii) to assess the homogeneity or heterogeneity of the amniotic fluid; (iii) to facilitate the prompt detection of meconium if, and when released into the amniotic fluid, and to notify and allow medical staff an opportunity to take appropriate steps to prevent further complications; and/or (iv) to otherwise detect the presence, and/or concentration of meconium at a plurality of locations of interest.

One example of a currently-preferred sensor arrangement is to locate one sensor in close proximity to the fetus' nose and mouth, since the presence of meconium in this area is likely to be of greatest concern. The other sensors 14 are preferably spaced relative to each other and to the first sensor in order to detect the presence of, and measure the concentration of meconium throughout the amniotic sac (or at least in the areas of most interest). Accordingly, a currently-preferred sensor arrangement contemplates locating a second sensor near the fetus' anus where the meconium would be released into the amniotic sac. In addition, a third sensor may be located at another position spaced between the first two sensors (e.g., in the amniotic fluid bathing the fetus' body between the anus and head). If the mother is lying on her back, then at least one of the sensors may be also located near the mother's back (or in a posterior location of the amniotic sac) where the amniotic fluid, and any meconium in the amniotic fluid, would tend to settle or collect due to gravitational forces. If, on the other hand, the mother is not lying on her back, then at least one sensor may be also located in another position where amniotic fluid, and any meconium in the amniotic fluid, would tend to settle or collect due to gravitational forces.

One advantage of the plural sensors of the invention is that they may be spaced relative to each other throughout the amniotic sac, and therefore the presence and location of meconium can be promptly identified. For example, if meconium is detected by a first sensor spaced away from the fetus' nose and mouth, but not by a second sensor located in close proximity to the nose and mouth, the medical staff may be provided sufficient time and opportunity to take appropriate steps to prevent the fetus from aspirating the meconium. Another advantage of the plural sensors of the invention is that if any one sensor becomes clogged, or otherwise rendered ineffective, the other sensors may continue to provide reliable data on the presence of, and concentration of meconium in the amniotic sac. In addition, the signals of the different sensors can be compared to each other to assess whether any sensor is generating inaccurate or erroneous data.

Figure 5:
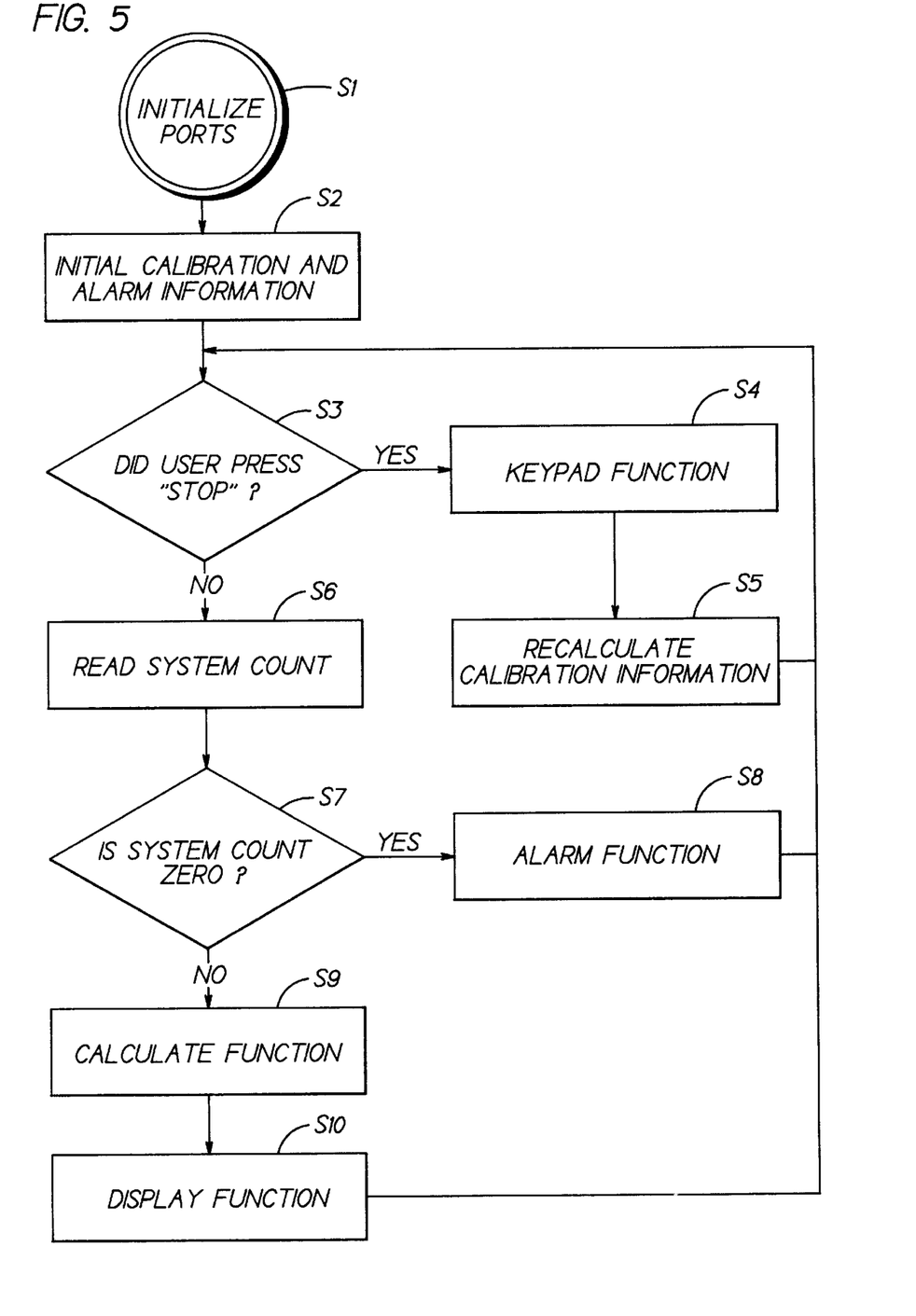
FIG. 5 is a flow chart, illustrating conceptually the procedural steps of a method of operating the apparatus of FIG. 1 in accordance with the present invention.

With reference to FIG. 5, prior to, or at the time of inserting and placing the sensors 14 at the select locations within the amniotic sac, the ports of the micro-controller 12 are initialized in order to delete any previously-displayed information and provide a clear display 18 (step S1). As indicated by step S2, the micro-controller 12 stores in its memory initial "calibration information" in order to calculate the concentration of meconium at each sensor site based on the transducer signals. The micro-controller 12 also stores in its memory "alarm information" in order to compare the calculated meconium concentration readings to a predetermined or preset alarm threshold. As is described further below, if the reading for any sensor exceeds its predetermined alarm threshold, an alarm signal is generated, which may be audible, visible (on the display 18), or both, to thereby alert the medical staff and simultaneously provide a real-time, continuous, qualitative and quantitative assessment of the concentration and location of meconium in the amniotic sac.

Figure 6:
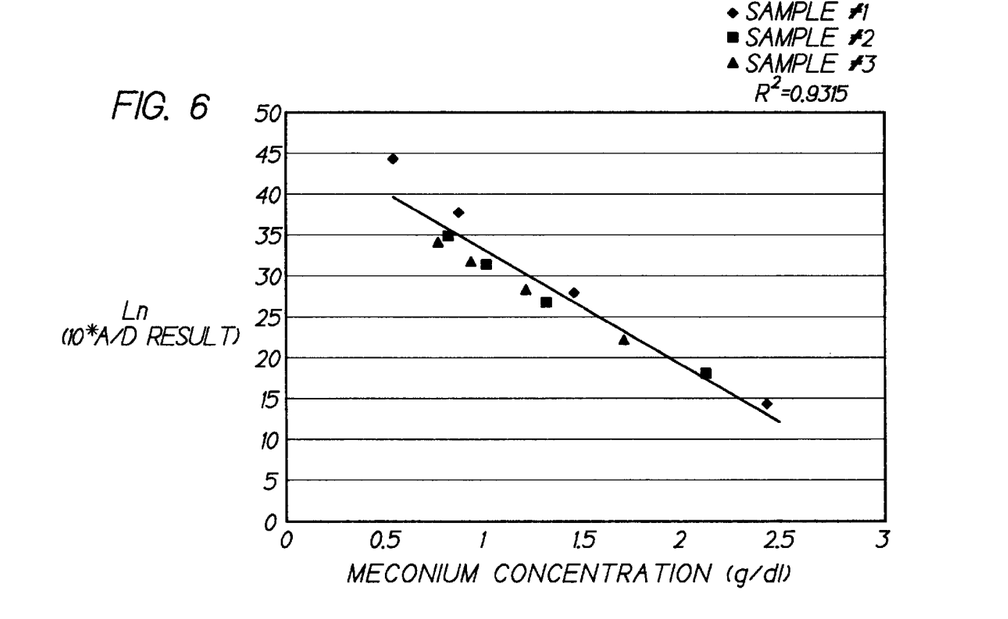
FIG. 6 is a graph illustrating the approximately linear relationship between the natural log of the signals generated by the sensors of the apparatus of FIG. 1, and the concentration of meconium in amniotic fluid.

It has been empirically determined that there is an approximately linear relationship between the natural log of the transducer signals, and the concentration of meconium in amniotic fluid. As one example, the graph of FIG. 6 shows an approximately linear relationship between the natural log of the transducer signals, and the meconium concentration (g/dl) for three different meconium samples dissolved in three different amniotic fluid samples. Accordingly, in accordance with a preferred embodiment of the invention, the micro-controller 12 converts each sensor signal from an analog to a digital signal, and calculates the natural log of the digital signal. Then, based on an approximately linear equation developed through empirical testing of the type illustrated in FIG. 6, the micro-controller 12 calculates the meconium concentration corresponding to each signal. In the currently-preferred embodiment of the invention, the relationship between the transducer signals and the meconium concentration level is defined by the following equation:

$$y = mx + b \quad (1)$$

wherein:
y is the natural log of the respective amplified, digital sensor signal;
m is the slope of the empirically determined linear relationship between the natural log of the sensor signals and the meconium concentration levels;
x is the meconium concentration level; and
b is the y-intercept.

In a currently-preferred embodiment of the invention, the slope "m" is approximately −14.22, and the y-intercept is approximately 46.87. Thus, after calculating the natural log of each sensor signal, the micro-controller 12 can calculate based on equation (1) the corresponding meconium concentration. Accordingly, as described further below and illustrated in FIG. 5, the apparatus 10 is preferably programmed to continuously calculate the natural log of each sensor signal, calculate based on the natural log and in accordance with equation (1) above the meconium concentration corresponding to the respective signal, and to display the calculated meconium concentration for each sensor signal.

Figure 7:
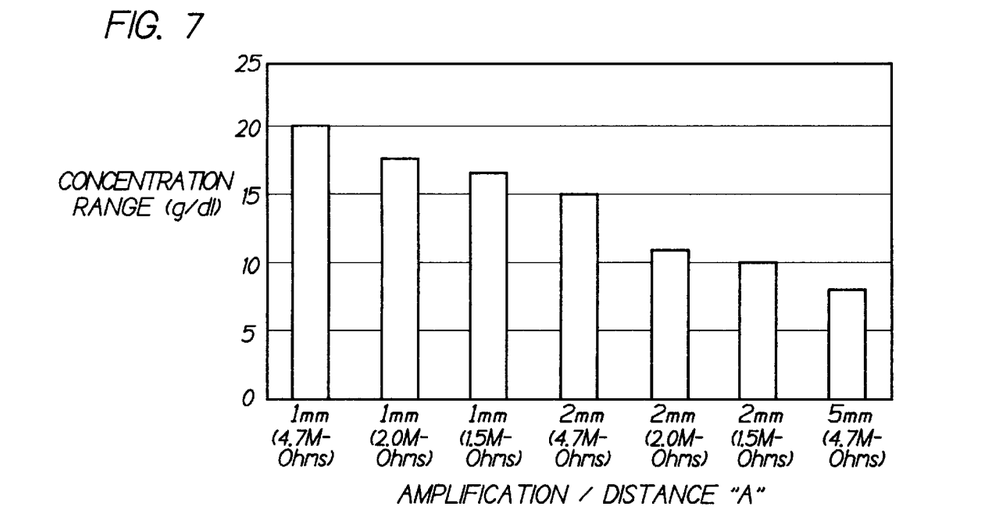
FIG. 7 is a graph illustrating the different ranges of meconium concentrations that may be detected by a typical sensor of the apparatus of FIG. 1 by adjusting the amplification of the sensor signal and the width of the amniotic fluid passageway between the light source and transducer of the sensor.

As may be recognized by those skilled in the pertinent art based on the teachings herein, it is important that the apparatus of the invention accurately detect the presence of, and/or concentration of meconium throughout a clinically relevant range of meconium concentrations. It has been determined that the clinically relevant range of meconium concentrations is between approximately 0 and 15 g/dl, and preferably between approximately 0 and 12 g/dl. This is the range where meconium concentrations progress toward potentially dangerous levels and throughout which the apparatus should be capable of accurately detecting the presence and concentration of meconium in the amniotic fluid. Accordingly, the sensitivity of each sensor 14 is preferably maximized over the clinically relevant range of meconium concentrations (approximately 0 through 12 g/dl). The amplified voltage signal transmitted by each transducer 22 defines a decaying exponential relationship with the concentration of meconium in the amniotic fluid passageway (i.e., the plot of the amplified voltage signals vs. the meconium concentration levels is a decaying exponential curve). The sensitivity of each sensor is maximized when detecting concentrations near the top of the decaying exponential curve. Accordingly, in order to maximize the sensitivity of the sensors in the clinically relevant range (0 through 12 g/dl), the amplification of the transducer signal and the distance "A" of the amniotic fluid passageway are preferably adjusted relative to each other to locate the clinically relevant range near the top of the decaying exponential curve. The amplification of each sensor signal can be altered by changing the size of the resistor in the respective amplifier circuit (i.e., the larger the resistor, the greater than gain). The chart of FIG. 7 shows the different ranges achieved for a typical sensor 14 of the apparatus of FIG. 1 by adjusting the size of the amplifier's resistor (1.5, 2.0 and 4.7 M-Ohm resistors), and the width of the amniotic fluid passageway "A" (1.0, 2.0 and 5.0 mm).

Turning again to FIG. 5, after reading the initial calibration and alarm information from memory, and before further proceeding, the micro-controller 12 checks to determine whether the user has instructed the micro-controller to "stop" (step S3). If "yes", then the user is permitted to reset the calibration information by inputting appropriate instructions through the keypad or like input device 30 (steps S4 and S5). For example, although the currently-preferred linear equation described above is believed to provide both a qualitative and quantitative assessment of the concentration of meconium in amniotic fluid, further empirical testing may generate different and/or additional data permitting the concentration of meconium to be more accurately determined. In addition, another and different embodiment of the invention, employing, for example, a different light source and/or transducer, or different auxiliary electronic components, may require different empirical data determined in the manner described above, or in a like manner, to thereby generate a different calibration curve to accurately convert the sensor signals to meconium concentration readings.

If the answer to the query of step 3 is "no", then the micro-controller 12 reads the "system count" and determines whether or not it is "zero" (steps S6 and S7). If the system count is "zero", then the meconium concentration readings displayed by the three respective groups of LEDs 32 of the display 18 are compared against the preset or predetermined alarm threshold (step S8). If any display reading exceeds the alarm threshold, the alarm signal is generated. If the system count is not "zero", then the meconium concentration value is calculated based on the respective sensor signal, and the calculated concentration value is displayed on the respective group of LEDs 32 of the display 18. In the currently-preferred embodiment of the invention, the "system count" is eight, i.e., the micro-controller calculates the meconium concentration levels corresponding to eight sensor signals before comparing the displayed concentration readings to the preset alarm threshold. However, as will be recognized by those skilled in the pertinent art based on the teachings herein, the system count can be changed to any of numerous different numbers for performing the functions described herein. As indicated in FIG. 5, the micro-controller 12 is programmed to operate in an endless loop of steps S6 through S10 until instructed to "stop" by the user, to thereby provide a continuous, real-time, qualitative and quantitative assessment of the presence of, and concentration of meconium in a plurality of locations within the amniotic sac.

Relevant portions of a currently-preferred embodiment of a computer program for controlling the operation of the apparatus 10 in accordance with the procedural steps of FIG. 5 are attached as an Appendix. As will be recognized by those of ordinary skill in the pertinent art, the program of the Appendix is written in the programming language "C", and can be downloaded into the memory of the micro-controller 12 by employing a cross compiler, such as the ImageCraft 68HC11 C Compiler. The ImageCraft program compiles the C program into an executable ".S19" file that can be transferred or downloaded into the memory of the micro-controller 12.

As will be recognized by those skilled in the pertinent art based on the teachings herein, numerous changes or modifications may be made to the above-described and other embodiments of the invention without departing from the scope of the invention as defined in the appended claims. For example, the apparatus of the invention may employ only a single sensor, or may employ a greater number of sensors than those shown. In addition, the type of light source and/or transducer employed for each sensor may be any of numerous different types of light sources and/or transducers that are currently known, or later become known to those skilled in the pertinent art for performing the functions described herein. If desired, a suitable filter or filtering mechanism may be provided on each sensor to prevent relatively large particulate matter from clogging the respective amniotic fluid passageway.

In addition, although the method and apparatus of the invention are described above in connection with detecting and assessing in vivo the concentration of meconium in amniotic fluid, they may be equally employed for in vitro detection and assessment of meconium concentrations. For example, the apparatus and method of the invention may be used for vaginal or intrauterine sampling of amniotic fluid, such as by inserting a sensor into any pools of amniotic fluid that may leak and collect in a vaginal area. In addition, amniotic fluid may be withdrawn and collected from one or more of the amniotic sac, intrauterine and/or vaginal areas and analyzed with one or more sensors outside of the body.

Accordingly, this detailed description of a preferred embodiment is to be taken in an illustrative, as opposed to a limiting sense.

What is claimed is:

1. An apparatus for measuring the concentration of meconium in amniotic fluid located within at least one of the intrauterine and vaginal areas of a patient, comprising:

at least one sensor insertable into at least one of the intrauterine and vaginal areas of the patient, the at least one sensor including a light source, a transducer facing the light source and spaced a predetermined distance therefrom, wherein the light source and transducer define an amniotic fluid passageway therebetween for receiving amniotic fluid therein upon insertion of the sensor into at least one of the intrauterine and vaginal areas, and the transducer generates first signals indicative of the amount of light from the light source transmitted through the amniotic fluid passageway and amniotic fluid therein, and received by the transducer; and a processor electrically coupled to the transducer for receiving the first signals therefrom, and generating based thereon second signals indicative of the concentration of meconium in the amniotic fluid received within the amniotic fluid passageway.

2. An apparatus as defined in claim 1, wherein the light source of the at least one sensor is a light-emitting diode having a transmission wavelength within the range of approximately 400 to 450 nm.

3. An apparatus as defined in claim 1, wherein the transducer of the at least one sensor includes a photodiode and operational amplifier for converting the light received from the light source to a voltage signal and amplifying the voltage signal respectively.

4. An apparatus as defined in claim 1, wherein the width of the amniotic fluid passageway defined between the light source and the transducer of the at least one sensor is within the range of approximately 1 through 5 mm.

5. An apparatus as defined in claim 1, wherein the processor is programmed to calculate the natural log of the first signal.

6. An apparatus as defined in claim 5, wherein the processor is programmed to calculate the second signal indicative of the meconium concentration based on the natural log of the first signal.

7. An apparatus as defined in claim 6, wherein the processor is programmed to calculate the second signal indicative of the meconium concentration based on an approximately linear relationship between the natural log of the first signal and the corresponding second signal.

8. An apparatus as defined in claim 1, wherein the processor is programmed to compare the second signal to a threshold meconium concentration, and generate an alarm signal if the second signal exceeds the meconium concentration threshold.

9. An apparatus as defined in claim 1, wherein the at least one sensor is capable of detecting the presence of, and concentration of meconium throughout a concentration range of approximately 0 through 12 g/dl.

10. An apparatus for measuring the concentration of meconium in amniotic fluid located within at least one of intrauterine and vaginal areas of a patient, comprising:

a plurality of sensors locatable in different positions within at least one of the intrauterine and vaginal areas of the patient, each of the plurality of sensors including a transducer, and an amniotic fluid passageway defined adjacent to the transducer for receiving amniotic fluid upon insertion of the sensor into at least one of the intrauterine and vaginal areas of the patient, wherein each sensor generates first signals indicative of the concentration of meconium in the amniotic fluid in the respective location of the sensor; and a processor electrically coupled to the plurality of sensors for receiving the first signals therefrom, and for generating second signals indicative of the concentration of meconium in the amniotic fluid at each sensor location.

11. An apparatus as defined in claim 10, wherein each sensor further includes a light source facing the transducer and spaced a predetermined distance therefrom.

12. An apparatus as defined in claim 11, wherein each sensor defines an amniotic fluid passageway between the respective sensor and light source, and the transducer generates first signals indicative of the amount of light from the light source transmitted through the amniotic fluid passageway and amniotic fluid therein and received by the transducer.

13. A method for measuring the concentration of meconium in amniotic fluid located within at least one of the intrauterine and vaginal areas of a patient, comprising the steps of:

provided at least one sensor including a light source for transmitting light and a transducer facing the light source for receiving the transmitted light;

spacing the transducer and light source a predetermined distance relative to each other to define an amniotic fluid passageway therebetween;

introducing the at least one sensor into at least one of the intrauterine and vaginal areas such that amniotic fluid therein will flow into the amniotic fluid passageway of the at least one sensor;

generating first signals indicative of the amount of light transmitted from the light source through the amniotic fluid passageway and received by the transducer; and generating second signals based on the first signals and indicative of the concentration of meconium in the amniotic fluid received within the amniotic fluid passageway.

14. A method as defined in claim 13, wherein the light source of the at least one sensor provides a transmission wavelength within the range of approximately 400 through 450 nm.

15. A method as defined in claim 13, further comprising the step of calculating the natural log of the first signal.

16. A method as defined in claim 15, wherein the second signal indicative of the meconium concentration is generated based on the natural log of the first signal.

17. A method as defined in claim 13, wherein the second signal is generated based on an approximately linear relationship between the natural log of the first signal and the corresponding second signal.

18. A method as defined in claim 13, further comprising the step of comparing the second signal to a threshold meconium concentration, and generating an alarm signal if the second signal exceeds the meconium concentration threshold.

19. A method for measuring the concentration of meconium in amniotic fluid located within at least one of the intrauterine and vaginal areas of a patient, comprising the steps of: providing a plurality of sensors insertable within at least one of the intrauterine and vaginal areas of the patient for generating signals indicative of the concentration of meconium in amniotic fluid in at least one of said areas;

inserting the plurality of sensors in a plurality of locations within at least one of the intrauterine and vaginal areas of the patient; and generating with the plurality of sensors a plurality of signals indicative of the concentration of meconium in the amniotic fluid in the plurality of locations.

20. A method as defined in claim 19, further comprising the step of placing at least one of the plurality of sensors adjacent to a fetus' nose or mouth.

21. A method as defined in claim 20, further comprising the step of placing at least one of the plurality of sensors adjacent to the fetus' anus.

22. A method as defined in claim 20, further comprising the step of placing at least one of the plurality of sensors in a location within at least one of the intrauterine and vaginal areas of the patient where amniotic fluid, and any meconium in the amniotic fluid, would tend to settle due to gravitational forces.

23. A method as defined in claim 19, comprising the step of providing a plurality of sensors, each sensor including a transducer, and a light source spaced a predetermined distance from the transducer and defining an amniotic fluid passageway therebetween.

24. A method as defined in claim 23, further comprising the step of generating first signals indicative of the amount of light from the light source transmitted through the amniotic fluid passageway and amniotic fluid therein and received by the transducer.

* * * * *